United States Patent [19]
Koizumi et al.

[11] Patent Number: 6,087,347
[45] Date of Patent: Jul. 11, 2000

[54] 3-SUBSTITUTED-D-HOMO-1,3,5 (10)-ESTRATRIENE DERIVATIVES

[75] Inventors: Naoyuki Koizumi, Sagamihara; Shigehiro Takegawa; Shigeki Iwashita, both of Kawasaki; Tomoko Kawachi, Nishinomiya; Mamoru Mieda, Ebina; Tomohito Fujii, Kawasaki, all of Japan

[73] Assignee: Teikoku Hormone Mfg. Co., Ltd., Japan

[21] Appl. No.: 09/254,734

[22] PCT Filed: Sep. 10, 1997

[86] PCT No.: PCT/JP97/03188

§ 371 Date: Mar. 12, 1999

§ 102(e) Date: Mar. 12, 1999

[87] PCT Pub. No.: WO98/11124

PCT Pub. Date: Mar. 19, 1998

[30] Foreign Application Priority Data

Sep. 12, 1996 [JP] Japan ................................ 8-262332

[51] Int. Cl.[7] ................. A61K 31/35; A61K 31/47; C07D 311/78; C07D 221/18
[52] U.S. Cl. ............... 514/80; 514/100; 514/284; 514/453; 546/23; 546/77; 549/220; 549/277; 549/384
[58] Field of Search ................. 549/277, 384, 549/220; 546/23, 77; 514/80, 100, 284, 453

[56] References Cited

U.S. PATENT DOCUMENTS 3,865,833  2/1975  Chorvat et al. .................. 546/77

FOREIGN PATENT DOCUMENTS

| 49-110670 | 10/1974 | Japan . |
| 51-13761 | 2/1976 | Japan . |
| 51-13761 | 7/1976 | Japan . |
| WO93/05064 | 3/1993 | WIPO . |

*Primary Examiner*—Bernard Dentz
*Attorney, Agent, or Firm*—Wenderoth, Lind & Ponack, L.L.P.

[57] ABSTRACT

Estratriene derivatives of the following formula have a powerful inhibitory effect on estrone sulfatase and are hence useful for the prophylaxis or treatment of diseases caused by estrogens, such as breast cancer, uterine cancer, ovarian cancer, endometriosis, adenomyosis uteri and mastopathy.

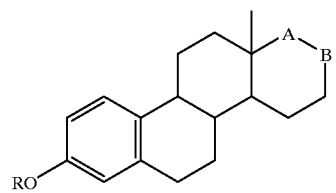

(I)

wherein one of A and B represents C=O or $CH_2$ and the other represents O or NH; and R represents $-SO_2NR^1R^2$ or $-PO(OM)_2$ in which $R^1$ and $R^2$ each independently represent a hydrogen atom or a lower alkyl group and M represents a hydrogen atom or an alkali metal; provided that, when one of A and B represents NH, the other represents C=O.

6 Claims, No Drawings

3-SUBSTITUTED-D-HOMO-1,3,5(10)-ESTRATRIENE DERIVATIVES

This application is a 371 of PCT/JP97/03188 filed Sep. 10, 1997.

TECHNICAL FIELD

This invention relates to novel 3-substituted-D-homo-1,3,5(10)-estratriene derivatives. More particularly, it relates to estratriene derivatives of the formula

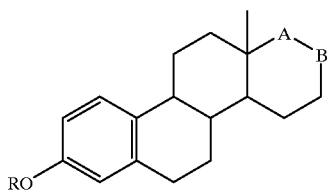

(I)

wherein one of A and B represents C=O or $CH_2$ and the other represents O or NH; and R represents $-SO_2NR^1R^2$ or $-PO(OM)_2$ in which $R^1$ and $R^2$ each independently represent a hydrogen atom or a lower alkyl group and M represents a hydrogen atom or an alkali metal; provided that, when one of A and B represents NH, the other represents C=O.

BACKGROUND ART

Estrone sulfate, which is an intermediate product in the steroid metabolism within the human body, is hydrolyzed by estrone sulfatase present in the living body to yield estrone in free form. It is also known that, in the living body, this estrone is further converted reversibly into estradiol by the action of 17β-hydroxysteroid dehydrogenase. These estrogens formed in the steroid metabolism, such as estrone and estradiol, are considered to be closely associated with diseases such as breast cancer, uterine cancer, ovarian cancer, endometriosis, adenomyosis uteri and mastopathy.

Accordingly, it is believed that, if the action of estrone sulfatase can be effectively inhibited, this would be effective for the treatment of diseases associated with estrogens. From this point of view, several compounds having an inhibitory effect on estrone sulfatase, as typified by estrone-3-sulfamate, have been proposed (see the pamphlet of International Publication of PCT Application No. WO93/05064).

However, estrone-3-sulfamate has the disadvantage that it causes an increase in liver weight as observed after the administration of estrogens.

It has now been found that novel 3-substituted-D-homo-1,3,5(10)-estratriene derivatives of the above formula (I) in which an oxygen or nitrogen atom is introduced into the D ring exhibit a powerful inhibitory effect on estrone sulfatase without causing an increase in liver weight.

Thus, the present invention provides estratriene derivatives of the above formula (I).

DISCLOSURE OF THE INVENTION

The term "lower" as used herein means that the groups or compounds modified by this term have not more than 6 carbon atoms and preferably not more than 4 carbon atoms.

In the above formula (I), examples of the "lower alkyl group" include methyl, ethyl, n-propyl, isopropyl, n-butyl, isobutyl, sec-butyl, tert-butyl and n-hexyl, and examples of the "alkali metal" include sodium and potassium.

Consequently, examples of the substituent group represented by R include $-SO_2NH_2$, $-SO_2NHCH_3$, $-SO_2NHC_2H_5$, $-SO_2NHC_3H_7$, $-SO_2N(CH_3)_2$, $-SO_2N(C_2H_5)_2$, $-PO(OH)_2$, $-PO(OH)(ONa)$, $-PO(ONa)_2$ and $-PO(OK)_2$.

A particularly preferred group of compounds represented by the above formula (I) is those of formula (I) in which R is $-SO_2NH_2$.

Moreover, a particularly preferred group of compounds represented by the above formula (I) is those of formula (I) in which A is C=O or $CH_2$ and B is O.

According to the present invention, compounds of the above formula (I) may be prepared by (a) reacting a compound of the formula

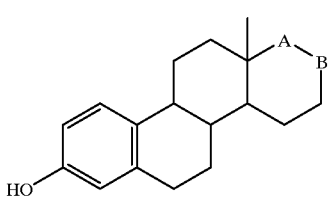

(II)

wherein A and B have the same meanings as described previously, with amidosulfonic acid chloride of the formula

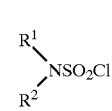

(III)

wherein $R^1$ and $R^2$ have the same meanings as described previously, or (b) reacting a compound of formula (II) with pyrophosphoric acid chloride and, if necessary, treating the reaction product with an alkali metal hydroxide (e.g., sodium hydroxide or potassium hydroxide).

The aforesaid reactions (a) and (b) may be carried out in an inert solvent selected, for example, from amides such as dimethylformamide and N-methylpyrrolidone, alkyl halides such as dichloromethane and dichloroethane, and organic bases such as pyridine, optionally in the presence of an alkali such as sodium hydride, sodium methoxide, potassium butoxide or potassium hydroxide, or an organic base such as triethylamine or 2,6-di-tert-butyl-4-methylpyridine, at a reaction temperature ranging from about −20° C. to the reflux temperature of the reaction mixture and preferably from about 0° C. to room temperature.

The proportion of amidosulfonic acid chloride or pyrophosphoric acid chloride to the compound of formula (II) may generally be such that amidosulfonic acid chloride or pyrophosphoric acid chloride is used in an amount of at least 1 mole, preferably 1.1 to 20 moles, and more preferably about 2 to 10 moles per mole of the compound of formula (II). Moreover, the aforesaid alkali is suitably used in an amount of about 2 to 10 moles per mole of the compound of formula (II).

The treatment with an alkali hydroxide in the aforesaid reaction (b) may be easily carried out by dissolving the reaction product in an aqueous solution of an alkali hydroxide according to the conventional method.

Thus, the compounds of the above formula (I) which are desired in the present invention can be formed.

Among the compounds of the above formula (II) which may be used as starting materials in the aforesaid reaction (a) or (b), those in which A is $CH_2$ are novel compounds which have not been described in the literature of the prior art. They may be prepared by reducing a compound of the above formula (II) in which A is C=O, or by subjecting 3,16α-dihydroxyestra-1,3,5(10)-trien-17-one to a reaction for introducing an oxygen atom into the D ring thereof. The details of the reaction conditions and the like are described in the Preparation Examples which will be given later.

The compounds of the above formula (I) which are formed according to the process of the present invention may be isolated and purified from the reaction mixture by per se known techniques such as recrystallization, distillation, column chromatography and thin-layer chromatography.

The above-described estratriene derivatives of formula (I) in accordance with the present invention have a powerful inhibitory effect on estrone sulfatase and are hence effective for the treatment of diseases associated with estrogens, such as breast cancer, uterine cancer, ovarian cancer, endometriosis, adenomyosis uteri, mastopathy, gynecomastia in the male, benign prostatic hyperplasia, and male infertility due to oligospermia.

The inhibitory effect of compounds of formula (I) on estrone sulfatase can be measured according to the following procedure.

(1) Measurement of an in vitro inhibitory effect on estrone sulfatase.

Intact MCF-7 human breast cancer cells were plated into 6-well plates (9.4 $cm^2$ per well) at $1 \times 10^5$ cells per well. Using a minimum essential medium (MEM) containing 5% fetal bovine serum, 2 mM glutamine and 0.22% sodium bicarbonate, the cells were grown until approximately 80% confluent.

The plates were washed with Earle's balanced salt solution (EBSS from Life Technologies Inc., Grand Island, N.Y., USA). Then, serum-free MEM (2 ml) containing 4 pmol ($4.4 \times 10^5$ dpm) of [6,7-$^3$H]estrone 3-sulfate (with a specific activity of 49 Ci/mmol; from New England Nuclear, Boston, Mass., USA) and a test compound was placed in each well of plates and incubated at 37° C. for 20 hours. After incubation, the plates were cooled, and the medium (1 ml) was transferred into a separating tube containing [4-$^{14}$C] estrone ($6 \times 10^3$ dpm) (with a specific activity of 52.5 mCi/mmol; from New England Nuclear, Boston, Mass., USA). This mixture, together with toluene (5 ml), was vigorously shaken for 30 seconds. It was shown by experiment that more than 90% of [4-$^{14}$C]estrone was removed from the aqueous layer by this treatment. A portion (2 ml) of the organic layer was taken and evaporated, and the $^3$H and $^{14}$C contents of the residue were measured by scintillation spectrometry. Then, the amount of estrone 3-sulfate hydrolyzed was calculated from the total $^3$H count (corrected for the volumes of the medium used and the organic phase, and for the recovery of the [$^{14}$C]estrone added) and the specific activity of the substrate.

As a result, 3-hydroxy-D-homo-17-oxaestra-1,3,5(10)-trien-17a-one 3-sulfamate (the compound of Example 1) and 3-hydroxy-D-homo-17-oxaestra-1,3,5(10)-triene 3-sulfamate (the compound of Example 2) inhibited the activity of estrone sulfatase by 92.1% and 93.7%, respectively, at a concentration of $10^{-9}$ M.

(2) Measurement of an in vivo inhibitory effect on estrone sulfatase

A test compound was dissolved in propylene glycol and administered, once a day, to a group of 5 female SD rats (body weight 168–194 g) for 5 days.

On the sixth day, all rats were sacrificed and dissected, and the liver was excised from each rat. The liver was finely minced with scissors, washed once with cold phosphate-buffered saline (PBS, pH 7.4), and resuspended in cold PBS (5 ml/g tissue). Under cooling with ice, the minced liver was homogenized with an Ultra-Turrax homogenizer. The resulting homogenate was centrifuged (at 4° C.) at 2,000×g for 30 minutes to remove nuclei and cell debris, and a portion (2 ml) of the supernatant was stored at −20° C. The protein concentration in this supernatant was measured according to the method of Bradford [Anal. Biochem., 72, 243–254 (1976)].

The supernatant in an amount corresponding to a protein concentration of 100 μg/ml was mixed with [6,7-$^3$H]estrone 3-sulfate (with a specific activity of 49 Ci/mmol; from New England Nuclear, Boston, Mass., USA) adjusted to a final concentration of 20 μM, in a final reaction volume made up to 1.0 ml with PBS. This reaction mixture was incubated at 37° C. for 30 minutes. After incubation (1 ml), the estrone sulfatase activity was determined in the same manner as described above for the in vitro measurement.

As a result, 3-hydroxy-D-homo-17-oxaestra-1,3,5(10)-triene 3-sulfamate (the compound of Example 2) inhibited the activity of estrone sulfatase by 99.3% at a dose of 0.5 mg/kg (p.o.).

Thus, the compounds of formula (I) in accordance with the present invention are useful as estrone sulfatase inhibitors and can hence be used for therapeutic purposes in human beings and other mammals by oral or parenteral administration (e.g., intramuscular injection, intravenous injection, intrarectal administration or percutaneous administration).

When the compounds of the present invention are used as drugs, they may be prepared in any of various pharmaceutical preparations according to the intended purpose. These pharmaceutical preparations include solid preparations (e.g., tablets, hard capsules, soft capsules, granules, powders, fine subtilaes, pills and troches), semisolid preparations (e.g., suppositories and ointments), and liquid preparations (e.g., injections, emulsions, suspensions, lotions and sprays). Non-toxic additives which can be used in the aforesaid pharmaceutical preparations include, for example, starch, gelatin, glucose, lactose, fructose, maltose, magnesium carbonate, talc, magnesium stearate, methylcellulose, carboxymethylcellulose and salts thereof, acacia, polyethylene glycol, alkyl esters of p-hydroxybenzoic acid, syrup, ethanol, propylene glycol, petrolatum, carbowax, glycerin, sodium chloride, sodium sulfite, sodium phosphate and citric acid. The aforesaid pharmaceutical preparations may also contain other therapeutically useful drugs.

The content of the compounds of the present invention in the aforesaid pharmaceutical preparations may vary according to the dosage form. Generally, it is desirable that solid and semisolid preparations contain the compounds of the present invention at a concentration of 0.1 to 50% by weight and liquid preparations contain them at a concentration of 0.05 to 10% by weight.

The dosage of the compounds of the present invention may vary widely according to the type of the warm-blooded animal (including human being) to be treated, the route of administration, the severity of symptoms, the diagnosis made by the doctor, and the like. Generally, they may be administered in a daily dose of 0.1 to 20 mg/kg and preferably 0.2 to 10 mg/kg. However, it is a matter of course that they may be administered in doses less than the lower limit of the aforesaid range or greater than the upper limit thereof, depending on the severity of symptoms in the patient and the diagnosis made by the doctor. The aforesaid daily dose may be given at a time or in several divided doses.

EXAMPLES

The present invention is more specifically explained with reference to the following examples and preparation examples.

Example 1

While 0.2 ml of chlorosulfonyl isocyanate was stirred under cooling with ice under an atmosphere of nitrogen, 0.086 ml of formic acid was added dropwise thereto. Thereafter, the resulting mixture was stirred at room temperature for 1 hour. After the addition of 0.2 ml of benzene, the reaction mixture was filtered through a Kiriyama funnel. The filtrate was concentrated to obtain 210 mg of sulfamoyl chloride.

After 120 mg of 3-hydroxy-D-homo-17-oxaestra-1,3,5(10)-trien-17a-one was dissolved in 0.5 ml of dimethylformamide and cooled with ice, a suspension of 100 mg of sodium hydride in 1 ml of dimethylformamide was added thereto, followed by stirring at room temperature for 30 minutes. Then, 200 mg of the previously synthesized sulfamoyl chloride was added thereto, followed by stirring at room temperature overnight. After water was added to the reaction mixture, the reaction product was extracted with ethyl acetate. The organic layer was washed with water and dried over magnesium sulfate. The solvent was distilled off, and the resulting crude product was purified by thin-layer chromatography (using a 9:1 mixture of chloroform and acetone as the developing solvent). 70 mg of the resulting amorphous substance was crystallized by adding 0.3 ml of diethyl ether and 3 drops of acetone under cooling with ice. Thus, there was obtained 13 mg of 3-hydroxy-D-homo-17-oxaestra-1,3,5(10)-trien-17a-one 3-sulfamate.

$^1$H-NMR (CDCl$_3$, δ): 1.25(3H, s), 4.1–4.6(2H, m), 7.05–7.16(2H, m), 7.33(1H, d, J=9 Hz). MS (m/z): 365(M$^+$), 286.

Example 2

The procedure of Example 1 was repeated by using 160 mg of D-homo-17-oxaestra-1,3,5(10)-trien-3-ol in place of 3-hydroxy-D-homo-17-oxaestra-1,3,5(10)-trien-17a-one. The resulting crude product was purified by thin-layer chromatography (using a 9:1 mixture of chloroform and acetone as the developing solvent) to obtain 89 mg of 3-hydroxy-D-homo-17-oxaestra-1,3,5(10)-triene 3-sulfamate.

$^1$H-NMR (CD$_3$OD, δ): 1.01(3H, s), 7.02–7.11(2H, m), 7.32(1H, d, J=9 Hz). MS (m/z): 351 (M$^+$).

Example 3

0.6 g of D-homo-17-oxaestra-1,3,5(10)-trien-3-ol was added to a mixture composed of 1 ml of pyrophosphoric tetrachloride and 12 ml of pyridine, and the resulting mixture was stirred at 0° C. for 3 hours under an atmosphere of nitrogen. The reaction mixture was poured into 500 ml of ice water, alkalified (pH 8.5) with a 10% aqueous solution of sodium hydroxide, and then acidified with 10% hydrochloric acid. The insoluble matter was separated by filtration, and suspended in 5 ml of water. After this suspension was adjusted to pH 9 with a 10% aqueous solution of sodium hydroxide, the insoluble matter was filtered off. 20 ml of ethanol was added to the filtrate, and the resulting mixture was allowed to stand in a refrigerator overnight. The precipitated crystals were collected by filtration, washed with cold ethanol, and dried to obtain 360 mg of 3-hydroxy-D-homo-17-oxaestra-1,3,5(10)-triene 3-phosphate disodium salt.

$^1$H-NMR (D$_2$O, δ): 0.98(3H, s), 3.17, 3.46(2H, ABq, J=11 Hz), 3.3–3.7(1H, m), 3.9–4.2(1H, m), 6.96(1H, br s), 7.00 (1H, br d, J=9 Hz), 7.27(1H, br d, J=9 Hz).

Example 4

The procedure of Example 1 was repeated by using 10 mg of 3-hydroxy-D-homo-17a-oxaestra-1,3,5(10)-trien-17-one in place of 3-hydroxy-D-homo-17-oxaestra-1,3,5(10)-trien-17a-one. The resulting crude product was purified by thin-layer chromatography (using a 19:1 mixture of chloroform and acetone as the developing solvent) to obtain 9 mg of 3-hydroxy-D-homo-17a-oxaestra-1,3,5(10)-trien-17-one 3-sulfamate.

$^1$H-NMR (DMSO-d$_6$, δ): 1.29(3H, s), 6.98–7.09(2H, m), 7.35(1H, d, J=9 Hz), 7.85(2H, br s). MS (m/z): 365(M$^+$), 286.

Example 5

The procedure of Example 1 was repeated by using 10 mg of D-homo-17a-oxaestra-1,3,5(10)-trien-3-ol in place of 3-hydroxy-D-homo-17-oxaestra-1,3,5(10)-trien-17a-one. The resulting crude product was purified by thin-layer chromatography (using a 19:1 mixture of chloroform and acetone as the developing solvent) to obtain 9 mg of 3-hydroxy-D-homo-17a-oxaestra-1,3,5(10)-triene 3 sulfamate.

$^1$H-NMR (CDCl$_3$, δ): 1.19(3H, s), 7.03–7.37(3H, m). MS (m/z): 351(M$^+$), 336, 272.

Example 6

The procedure of Example 1 was repeated by using 20 mg of 3-hydroxy-17a-aza-D-homoestra-1,3,5(10)-trien-17-one in place of 3-hydroxy-D-homo-17-oxaestra-1,3,5(10)-trien-17a-one. The resulting crude product was recrystallized from chloroform-methanol to obtain 7 mg of 17a-aza-3-hydroxy-D-homoestra-1,3,5(10)-trien-17-one 3-sulfamate.

$^1$H-NMR (DMSO-d$_6$, δ): 1.09(3H, s), 6.9–7.1(2H, m), 7.32(1H, d, J=9 Hz), 7.51(1H, s), 7.84(2H, s). MS (m/z): 364(M$^+$), 349, 285, 270.

Preparation Example 1

286 mg of 3-hydroxy-D-homo-17-oxaestra-1,3,5(10)-trien-17a-one was suspended in 2.5 ml of tetrahydrofuran, and 400 mg of lithium tri-t-butoxy-aluminohydride was added thereto under cooling with ice, followed by stirring for 30 minutes under cooling with ice. After water and 5% hydrochloric acid were added to the reaction mixture, the reaction product was extracted with ethyl acetate. The organic layer was washed with water and dried over magnesium sulfate. Thereafter, the solvent was distilled off to obtain 324 mg of D-homo-17-oxaestra-1,3,5(10)-triene-3,17aζ-diol.

$^1$H-NMR (CD$_3$OD, δ): 0.92(3H, s), 6.47–6.60(2H, m), 7.06(1H, d, J=8 Hz). MS (m/z): 288(M$^+$), 214.

Preparation Example 2

264 mg of D-homo-17-oxaestra-1,3,5(10)-triene-3,17aζ-diol was suspended in 7 ml of dichloromethane under an atmosphere of nitrogen. While the resulting suspension was cooled with ice, 0.24 ml of triethylsilane and 0.14 ml of boron trifluoride etherate were added thereto, followed by stirring for 20 minutes under cooling with ice. After a saturated aqueous solution of sodium hydrogen carbonate was added to the reaction mixture, the resulting mixture was allowed to warm to room temperature and the reaction product was extracted with ethyl acetate. The organic layer was washed with a saturated aqueous solution of sodium hydrogen carbonate and then with water. After the organic layer was dried over magnesium sulfate, the solvent was distilled off, and the resulting crude product was purified by thin-layer chromatography (using a 9:1 mixture of chloroform and acetone as the developing solvent) to obtain 164 mg of D-homo-17-oxaestra-1,3,5(10)-trien-3-ol.

$^1$H-NMR (CDCl$_3$, δ): 1.01(3H, s), 3.05, 3.48(2H, ABq, J=11 Hz), 3.3–3.6(1H, m), 4.0–4.2(1H, m), 6.56–6.68 (2H, m), 7.15(1H, d, J=8 Hz). MS (m/z): 272(M$^+$).

Preparation Example 3

To a mixture composed of 167 mg of 3,16α-dihydroxyestra-1,3,5(10)-trien-17-one and 1 ml of dioxane, a mixture composed of 155 mg of orthoperiodic acid and 0.55 ml of water was added under cooling with coater, followed by stirring for 1 hour. After water was added to the reaction mixture, the reaction product was extracted with ethyl acetate. The organic layer was washed with water and dried over magnesium sulfate. The solvent was distilled off, and the resulting crude product was purified by thin-layer chromatography (using a 4:1 mixture of chloroform and acetone as the developing solvent) to obtain 107 mg of 3-hydroxy-16-oxo-16,17-secoestra-1,3,5(10)-trien-17-oic acid.

$^1$H-NMR (DMSO-d$_6$, δ): 1.04(3H, s), 6.3–6.7(2H, m), 7.02 (1H, d, J=8 Hz), 9.44(1H, br).

Preparation Example 4

A mixture composed of 36.4 g of 3-hydroxy-16-oxo-16,17-secoestra-1,3,5(10)-trien-17-oic acid, 1 liter of dioxane, 1 liter of tetrahydrofuran, and 10 g of lithium aluminum hydride was stirred for 5 hours under cooling with water. After 5% hydrochloric acid was added to the reaction mixture, the reaction product was extracted with ethyl acetate. The organic layer was washed with water and dried over magnesium sulfate. Thereafter, the solvent was distilled off to obtain 29.2 g of 16,17-secoestra-1,3,5(10)-triene-3,16,17-triol.

A mixture composed of 29.2 g of 16,17-secoestra-1,3,5(10)-triene-3,16,17-triol, 1.0 g of p-toluenesulfonic acid, and 500 ml of toluene was slowly distilled. After a 5% aqueous solution of sodium hydrogen carbonate was added to the reaction mixture, the organic layer was washed with water and dried over magnesium sulfate. The solvent was distilled off, and the resulting crude product was purified by column chromatography (using a 50:1 mixture of chloroform and acetone as the eluting solvent) to obtain D-homo-17-oxaestra-1,3,5(10)-trien-3-ol.

What is claimed is:

1. An estratriene derivative of the formula

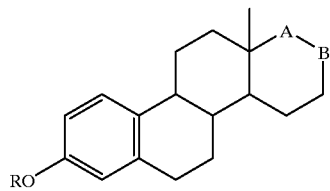

wherein one of A and B represents C=O or CH$_2$ and the other represents O or NH; and R represents —SO$_2$NR$^1$R$^2$ or —PO(OM)$_2$ in which R$^1$ and R$^2$ each independently represent a hydrogen atom or a lower alkyl group and M represents a hydrogen atom or an alkali metal; provided that, when one of A and B represents NH, the other represents C=O.

2. An estratriene derivative as claimed in claim 1 wherein R represents —SO$_2$NH$_2$.

3. An estratriene derivative as claimed in claim 1 wherein one of A and B represents C=O or CH$_2$ and the other represents O.

4. An estrone sulfatase inhibitor containing the compound of claim 1.

5. A pharmaceutical composition comprising the compound of claim 1 and a pharmaceutically acceptable additive.

6. A method for the prophylaxis or treatment of a disease caused by estrogens in a human being or other mammal which comprises administering the compound of claim 1 to the human being or other mammal.

* * * * *